United States Patent [19]

Gundlach

[11] Patent Number: 5,024,325
[45] Date of Patent: Jun. 18, 1991

[54] PREWETTED ABSORBENT PADS AND DISPENSING PACKAGE THEREFOR

[75] Inventor: Douglas P. Gundlach, Midland, Mich.

[73] Assignee: DowBrands Inc., Indianapolis, Ind.

[21] Appl. No.: 465,854

[22] Filed: Jan. 16, 1990

[51] Int. Cl.⁵ .................... A45D 35/00; A61M 35/00
[52] U.S. Cl. ............................ 206/229; 206/361; 206/362; 206/438; 604/310; 401/130; 15/104.54
[58] Field of Search ................ 206/361, 362, 438; 604/310; 401/130; 15/104.94

[56] References Cited

U.S. PATENT DOCUMENTS

| | | |
|---|---|---|
| 866,243 | 9/1907 | Waechter . |
| 1,973,903 | 9/1934 | King . |
| 2,613,011 | 10/1952 | Foreshaw-Smith . |
| 2,983,369 | 5/1961 | Rogovin . |
| 3,299,464 | 1/1967 | O'Bren et al. ............ 206/229 |
| 4,258,849 | 3/1981 | Miller . |
| 4,641,391 | 2/1987 | De brey . |
| 4,893,956 | 1/1990 | Wojcik et al. ............ 206/229 |

Primary Examiner—Joseph M. Moy

[57] ABSTRACT

A dispensing package for dispensing discrete portions of a vaporizable material in the form of prewetted absorbent pads, wherein the dispensing package broadly comprises a container and a plurality of such absorbent pads. The absorbent pads are closely stacked within the container, and generally comprise an absorbent pad portion with a flexible film backing which is resistant to permeation of the vaporizable material therethrough, and a collapsible tab- or ring-like structure joined to the backing opposite the absorbent pad portion. In other embodiments, the absorbent pad portion is preferably sub-divided into sub-portions having different fluid absorbing characteristics, which sub-portions are separated by the same flexible film as used in the backing, and less than all of the sub-portions are initially prewetted with the vaporizable material or are prewetted with different materials.

7 Claims, 1 Drawing Sheet 5,024,325

PREWETTED ABSORBENT PADS AND DISPENSING PACKAGE THEREFOR

FIELD OF THE INVENTION

This invention relates to absorbent pads for applying and/or removing selected materials to and/or from a given surface, and more particularly but without limitation, to absorbent pads for applying and/or removing materials which are subject to evaporation when stored under normal conditions preparatory to use with such absorbent pads. In another significant aspect, the invention relates to dispensing packages for dispensing discrete portions of such vaporizable materials by means of such absorbent pads.

BACKGROUND OF THE INVENTION

Absorbent pads, and in particular prewetted absorbent pads, have become popular vehicles for the delivery, application and removal of various products in recent years. Such pads are used today to deliver, apply, and remove antiseptic lotions, skin medications, cosmetics, soaps and other cleaning products, for example. Many of these products contain alcohols, ammonia, and volatile solvents and are thus subject to evaporative losses when stored under normal conditions preparatory to use.

Usually these absorbent pads, and "absorbent pads" as used herein includes the towelette type products used for diaper wipes, wet napkins, applicators for furniture and shoe polish, and similar type uses, have been sold premoistened or prewetted in individual packages or stacked in containers having a lid to be opened and closed by the consumer. The drawbacks which are most often associated with having each pad individually wrapped are the expense to the manufacturer and to the consumer of individually packaging what would otherwise be a much less expensive product, perhaps, and the inconvenience of having to open a new package with every new use of the pads. One advantage of individually wrapping these products, however, is that loss of the useful material absorbed into the pads by evaporation during storage is minimized. In many cases, however, the losses which might otherwise be experienced due to evaporation will not justify the added expense associated with packaging and the added inconvenience to consumers.

The other conventional method of packaging absorbent pads preparatory to their use by the consumer has been to stack the pads in containers having reclosable lids. The difficulty with this sort of dispensing package is that, for those materials carried by the absorbent pads which are subject to evaporation under normal storage conditions, evaporative losses are often unacceptably high. The consumer in using the pads from such containers may not close the lid, or may not close the lid properly, or may be unable to close the lid sufficiently to obtain a good seal. Moreover, as are removed from certain of these containers, used and discarded, the space between the remaining pads and the lids thereof may provide increasing room for evaporation of material from the remaining pads. This material will be lost when such a container is next opened, even if the container is properly closed and resealed after each such use.

There is a need, then, for a dispensing package of prewetted or premoistened absorbent pads in particular which provides a degree of resistance to losses by evaporation of useful, vaporizable materials superior to that provided by the lidded containers described above, but which does not make the pads inconvenient to use or add appreciably to packaging costs.

The present invention meets this need and overcomes the shortcomings of the prior art in providing a novel and improved absorbent pad and a novel dispensing package for dispensing discrete portions of a vaporizable material for a variety of uses.

SUMMARY OF THE INVENTION

The dispensing package of the present invention comprises a container and a plurality of absorbent pads which have been prewetted with a vaporizable material and held in a stack close fitting the interior walls of the container. Each of the absorbent pads comprises an absorptive material, a backing for at least a portion of the absorptive material, and means joined to the backing opposite the portion of the absorptive material for manually manipulating the pad.

The novel and improved absorbent pads of the present invention are broadly described as comprising: an absorbent pad portion containing at least one absorptive material, and having at least two discrete sub-portions separated by a barrier to the vaporizable material held in the absorbent pad portion: a backing for at least a part of the absorbent pad portion, which backing is resistant to permeation of the vaporizable material therethrough: and, means joined to the backing opposite the part of the absorbent pad portion for manually manipulating the pad.

DETAILED DESCRIPTION OF THE PREFERRED EMBODIMENTS

Figure 1:
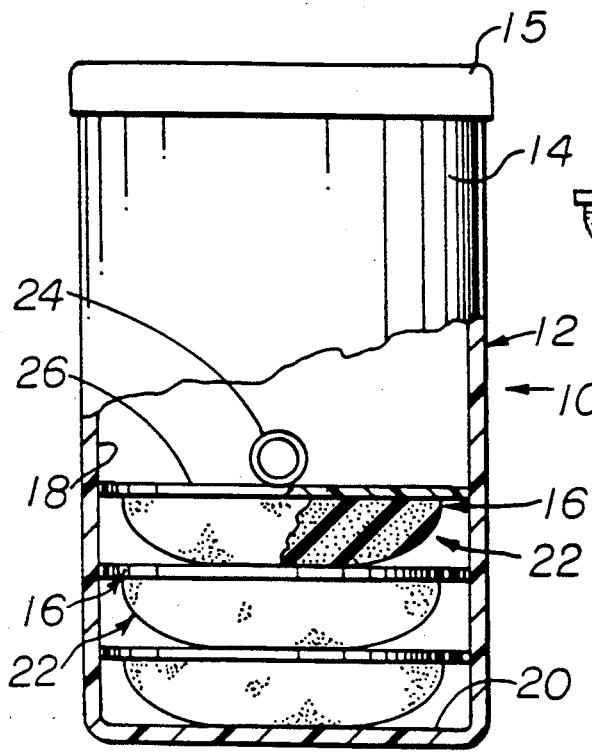
FIG. 1 is a view in section of a dispensing package of the present invention, showing a container and absorbent pads held therein.

Referring now to the drawings, and more particularly to FIG. 1, the dispensing package of the present invention is shown and generally designated by the numeral 10. As shown in FIG. 1, the dispensing package 10 preferably comprises a container 12 having a top portion 14 optionally including a lid 15 (in dashed outline) which may be opened to provide easy access to pads 16 held in the container 12, the pads 16 preferably being prewetted or premoistened for storage in the container 12 preparatory to their use by the consumer.

Although the top portion 14 may be so constructed, where the dispensing package is in accordance with the teachings of the present invention, it should not ordinarily be necessary that the top portion 14 of the container 12 be resealable to provide adequate resistance to evaporative losses of the vaporizable material held by the pads 16. In preferred embodiments of the dispensing package of the present invention, the dispensing package 10 will be open-topped or the top portion 14 will be at least partially open to the atmosphere, as by having a film stretched across the top portion 14 with a slitted opening in the manner of boxes of facial tissues, for example. In this way, the consumer need not be concerned with some sort of lid or resealable closure which the consumer may not remember to use or may not be able to use effectively, and access to the pads 16 is convenient and immediate.

As may be readily seen in FIG. 1, the pads 16 are preferably stacked in the container 12 with little if any clearance between the perimeter of the pads 16 and the interior walls 18 and bottom 20 of the container 12, and with little or no space between adjacent pads 16. Pads 16 can be of a circular, oval, rectangular or other shape, provided, however, that to ensure that little if any clearance exists between the perimeter of the pads 16 and the interior walls 18 of the container 12, the pads 16 are shaped similar to the interior of the container 12. Because the pads 16 are in preferred embodiments of the present invention adapted to hold in their absorbent pad portions 22 discrete portions of a given vaporizable material and are preferably prewetted with such material, there is no need or advantage to allowing a pool of the material to form in the container 12 to moisten the pads 16 for use as has been practiced previously. See, e.g., U.S. Pat. Nos. 2,613,011 and 2,983,369. Rather, the pads 16 are preferably given only a sufficient clearance with respect to the walls 18 to permit their ready and convenient removal from the container 12 by accessing finger-engaging tab- or ring-like projections 24 or their equivalents from backings 26 of each of the pads 16 in turn. In the described manner of construction, the amount of free vaporizable material which can evaporate, and the avenues of evaporation from the pads 16 through the container 12 are reduced.

Figure 2:
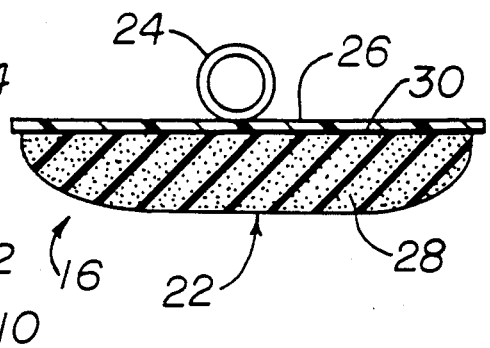
FIG. 2 is a view in section of one embodiment of the absorbent pads of the present invention.

The pads 16 may preferably be constructed according to the alternative embodiments shown in FIGS. 2–5. In the embodiment shown in FIG. 2, a pad 16 comprises an absorptive material 28 such as a nonwoven cellulosic material accumulated in an absorbent pad portion 22, a backing 26 in the form of a flexible film such as a low density polyethylene film of about 3 mils in thickness covering a surface 30 and preferably covering substantially all of a surface 30 of the absorbent pad portion 22, and means for manually manipulating the pad 16 in the form of a pivotably held tab- or ring-like projection 24 which may be collapsed against the backing 26 when not in use. In FIG. 2, a ring-like projection is shown.

Figure 3:
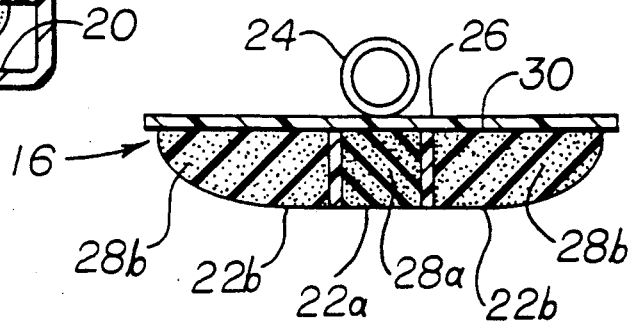
FIG. 3 is a view in section of an alternative embodiment of the pads of the present invention.
Figure 5:
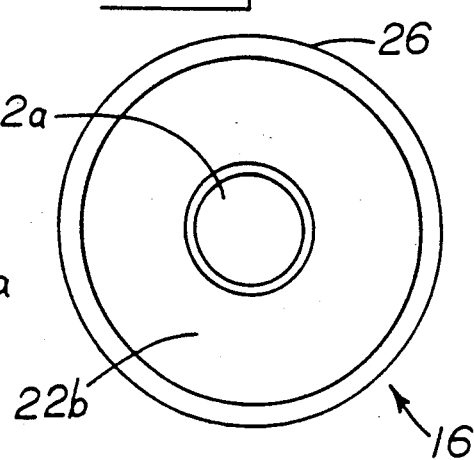
FIG. 5 is a bottom view, in full, of another embodiment of the pads of the present invention.
Figure 4:
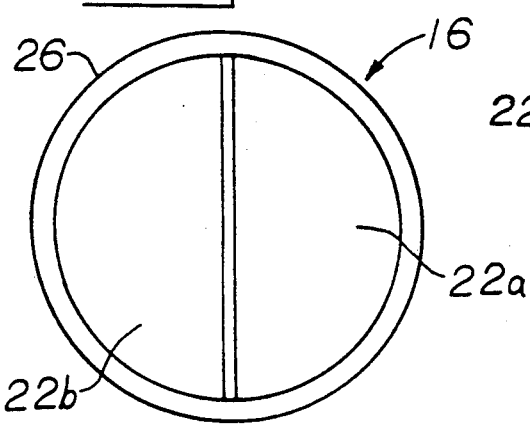
FIG. 4 is a bottom view, in full, of the alternative embodiment shown in FIG. 3.

The alternative embodiments of the pads 16 which are shown in FIGS. 3–5 differ from the embodiment shown in FIG. 2 in the division of the absorbent pad portion 22 into a first sub-portion 22a including a first absorptive material 28a and a second sub-portion 22b including a second absorptive material 28b, with the first sub-portion 22a and the second sub-portion 22b being preferably separated by the same permeation-resistant flexible film material which comprises the backing 26 of the pads 16 of the preferred embodiment of the present invention, although clearly other film materials and permeation-resistant film materials, particularly, can be used.

In the alternative embodiment shown in FIGS. 3 and 4, the first sub-portion 22a is surrounded by the second sub-portion 22b, although other configurations utilizing a plurality of sub-portions can be employed as well. For example, and looking only at possible permutations of the pad having only two as opposed to several distinct sub-portions, instead of the first sub-portion 22a being surrounded by the second sub-portion 22b the sub-portions 22a and 22b could be placed in side-by-side relation, as shown in FIG. 5. Or, the first and second sub-portions could each be wetted with the same or different materials. The first and second absorptive materials could be the same or different, and could have the same or different affinities with regard to a given vaporizable material. Also, one of the respective sub-portions could be wetted while the other is not. Whether one of these other constructions might be desirable depends, of course, on the intended use of the pads of the present invention.

In using the dispensing package, the pads 16 will, as noted earlier, preferably be closely stacked within a container 12 which may be overwrapped in a permeation resistant material when purchased. In use, the consumer will remove any protective outer wrap, grasp the tab- or ring-like projection 24 from the backing 26 of the uppermost pad 16, remove the pad 16 and by placing the absorbent pad portion 22 of the pad 16 into contact with a selected surface with pressure on the backing 26 of the pad 16, deliver and apply the vaporizable material theretofore held by the pad 16 to the surface. By means of the ring-like projection 24, then, the user may move the pad 16 to distribute the vaporizable material or to work the material into the surface by rubbing or scrubbing and the like. By the substantial release of pressure or the use of very light pressure upon the backing 26, and with most absorptive materials, reabsorption and removal of at least a portion of the vaporizable material delivered and perhaps of other materials as well can be expected before the pad 16 is discarded.

It is with this last utility in mind that the alternative embodiments of the pads 16 have been provided With the alternative embodiments, it is expected that the ability of a consumer to apply a given material to a surface and to thereafter remove a portion at least of that material will be enhanced, compared to what would be possible with a uniformly constructed and moistened pad 16. One may also, with the provision of two absorbent materials as opposed to a single absorbent material, take into account any change in the character or nature of the material to be reabsorbed after application and use of the original vaporizable material.

For example, a liquid soap concentrate might be carried in the first sub-portion 22a of the absorbent pad portion 22, with nothing in the larger second sub-portion 22b initially. On use of the pad 16 and the soap concentrate to clean a surface with water, the remaining liquid after cleaning may have more of the character of water and might have a greater affinity for another material than that which originally carried the soap concentrate. It would then be desirable to have employed this other material as the second absorptive material within the second sub-portion 22b of the absorbent pad portion 22 of the pad 16.

The construction of the remaining pads and of the container may be seen to be of material advantage in terms of reducing evaporative losses from lower pads after the first or uppermost pad has thus been used, at least with respect to the lidded containers of the prior art. The matching of an absorptive material or materials, depending on which embodiment of the pads 16 of the present invention is employed, with the nature and quantity of the vaporizable material to be carried by the pads 16 will help to hold the vaporizable material in a useful condition.

Further, the backing 26 if properly selected will form a barrier to the permeation or diffusion of the material from each pad 16 and lower pads 16 upward and out of the container 12. Finally, the close tolerances within the container 12, while not allowing the wetting of the pads 16 by any free liquid or any liquid from lower pads 16, also render the barriers to evaporation posed by the series of backings 26 and absorbent pad portions 22 above more effective. It can be seen also that one alternative embodiment of the preferred pads 16 of the present invention, in placing a flexible permeation-resistant film around the vaporizable material carried in the first sub-portion 22a, adds still another barrier to evaporative losses of the vaporizable material from a pad 16.

The provision of a flexible film backing 26 and tab- or ring-like projection 24 for each preferred pad 16, in combination with the proper matching of the absorbent material or materials of the absorbent pad portion 22 confers an additional benefit in terms of the use of the pads 16 as well, in that the user can apply a vaporizable material to a given surface without coming directly into contact with the bulk of the material contained in the pad 16 being used. Some exposure may be expected from the contact of the absorbent pad portion 22 of the pad 16 immediately above with the backing 26 of the pad 16 to be used, but this may be lessened again by matching the absorptive material used for constructing the pads 16 with the nature and quantity of material to be carried by a pad 16.

In any event, it is considered that the amounts of the vaporizable material with which one would come into contact in using the dispensing package of the present invention should be less than that encountered with those pads of the prior art which are wetted by a wicking action and exposure to free flowing material.

While specific embodiments of the present invention have been described for purposes of this disclosure, numerous changes in the construction and arrangement of parts can be made without departing in scope or spirit from the present invention, as defined by the appended claims.

What is claimed is:

1. An absorbent pad for the application and/or removal of a vaporizable material to and/or from a selected surface, comprising:
    an absorbent pad portion containing at least one absorptive material, and having at least two discrete sub-portions separated by a flexible barrier to said vaporizable material;
    a backing for at least a part of said absorbent pad portion, wherein said backing is resistant to permeation of said vaporizable material therethrough; and
    means joined to said backing for manually manipulating the pad.

2. A pad as defined in claim 1, wherein said backing comprises a flexible film which is resistant to permeation of said vaporizable material therethrough.

3. A pad as defined in claim 1, wherein said absorbent pad portion comprises a first sub-portion including a first absorptive material surrounded by a second sub-portion including a second absorptive material.

4. A pad as defined in claim 3, wherein said first and second absorptive materials have differing affinities for said vaporizable material.

5. A pad as defined in claim 1, wherein said absorbent pad portion comprises a first sub-portion including a first absorptive material in side-by-side relationship to a second sub-portion including a second absorptive material.

6. A pad as defined in claim 5, wherein said first and second absorptive materials have differing affinities for said vaporizable material.

7. A dispensing package for dispensing discrete portions of a vaporizable material, comprising:
    a container; and
    a plurality of absorbent pads which have been prewetted with the vaporizable material and held in a stack close-fitting the interior walls of said container, wherein said absorbent pads each comprise:
    an absorbent pad portion containing at least one absorptive material, and having two or more discrete sub-portions separated by a barrier to said vaporizable material;
    a backing for at least a portion of said absorptive material; and
    means joined to said backing for manually manipulating said pad.

* * * * *